United States Patent
Sasa (10) Patent No.: US 7,024,041 B2
(45) Date of Patent: Apr. 4, 2006

(54) PATTERN INSPECTION APPARATUS AND METHOD

(75) Inventor: Yasushi Sasa, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 758 days.

(21) Appl. No.: 10/216,320

(22) Filed: Aug. 12, 2002

(65) Prior Publication Data

US 2003/0031356 A1 Feb. 13, 2003

(30) Foreign Application Priority Data

Aug. 13, 2001 (JP) ............................. 2001-245354

(51) Int. Cl.
*G06K 9/68* (2006.01)

(52) U.S. Cl. ..................................... 382/221
(58) Field of Classification Search ................ 382/219, 382/221

See application file for complete search history.

(56) References Cited

U.S. PATENT DOCUMENTS

| | | | | |
|---|---|---|---|---|
| 5,912,988 | A * | 6/1999 | Moore ......................... | 382/209 |
| 6,178,257 | B1 * | 1/2001 | Alumot et al. ............... | 382/145 |
| 2002/0039436 | A1 * | 4/2002 | Alumot et al. ............... | 382/149 |
| 2002/0085237 | A1 * | 7/2002 | Bradburn ..................... | 358/3.27 |
| 2002/0093686 | A1 * | 7/2002 | Fan et al. ..................... | 358/3.08 |

FOREIGN PATENT DOCUMENTS

| | | |
|---|---|---|
| JP | 6-21769 | 3/1994 |
| JP | 2000-065545 | 3/2000 |

* cited by examiner

*Primary Examiner*—Jingge Wu
*Assistant Examiner*—Robert Tarcu
(74) *Attorney, Agent, or Firm*—McDermott Will & Emery LLP (57) ABSTRACT

A marginal distribution feature extraction unit 20 sequentially focuses on each pixel in a reference image and the corresponding pixel in an inspection image, and computes a marginal distribution feature value indicative of the spatial variation in pixel values in the focus pixel neighborhood in both images. Based on this marginal distribution feature value, a tolerance image generation selection unit 26 sets a tolerance range for the reference image or inspection image focus pixel with the less spatial variation. A target image selection unit 30 selects the image comprising pixels from both images for which a tolerance range is not set as a target image. Referencing the set tolerance ranges, a comparison operator 34 compares each pixel in the target image and tolerance image, and outputs a difference Sub representing how far the pixel values of the target image are from the respective tolerance range. A defect determination circuit 38 then outputs data indicating the pixels corresponding to a defect based on a difference map containing these difference Sub values.

10 Claims, 9 Drawing Sheets

PATTERN INSPECTION APPARATUS AND METHOD

BACKGROUND OF THE INVENTION

1. Field of the Invention

The present invention relates generally to a pattern inspection apparatus for inspecting a pattern and detecting defects appearing in the external shape of various inspected objects, and relates more specifically to a pattern inspection apparatus for inspecting patterns on high resolution printed wiring boards, lead frames, semiconductor wafers, and the like and photomasks therefor, and detecting minute defects therein.

2. Description of the Related Art

One method of inspecting patterns on high precision printed wiring boards, lead frames, semiconductor wafers, and the like and photomasks therefor is the comparative method. This method detects defects in an inspected object by comparing the values of positionally corresponding pixels (referred to below as simply "corresponding pixels") in a reference image representing a good pattern with no defects and the inspection image representing the pattern on the inspected object. When this comparative method uses a multivalued image for pattern inspection, detection errors can occur due to error in the sampling position when the image is captured (referred to below as "image sampling error"). More specifically, even if a difference between compared pixel values in the reference image and inspection image is detected, it is not known whether this difference is due to an actual defect or to the effects of this image sampling error, and parts that are not actually defects are falsely detected as defects.

Japanese Patent Laid-Open Publication (kokai) 2000-65545 teaches a pattern inspection method as a solution to this problem. This pattern inspection method expands the digital image defect detection method taught in Japanese Patent Publication (kokoku) H6-21769 (U.S. Pat. No. 4,803,734 corresponds to Publication H6-21769 and is incorporated herein by reference) for application to multivalued images by setting a pixel value range with width for the value of each pixel in the reference image. This pixel value range is applied as an allowable difference range (referred to below as the "tolerance range") for determining if the values of corresponding pixels in the reference image and inspection image are the same. Using this method a pixel in the inspection image is deemed to match the corresponding pixel in the reference image if its pixel value is within the pixel value range of the corresponding pixel in the reference image, and parts where these values match are deemed to not be a defect. This makes it possible to prevent overdetection (falsely detecting parts that are not defects to be defects) due to sampling error in parts where there is great variation in pixel values, such as at the edge parts of an image.

Figure 7:
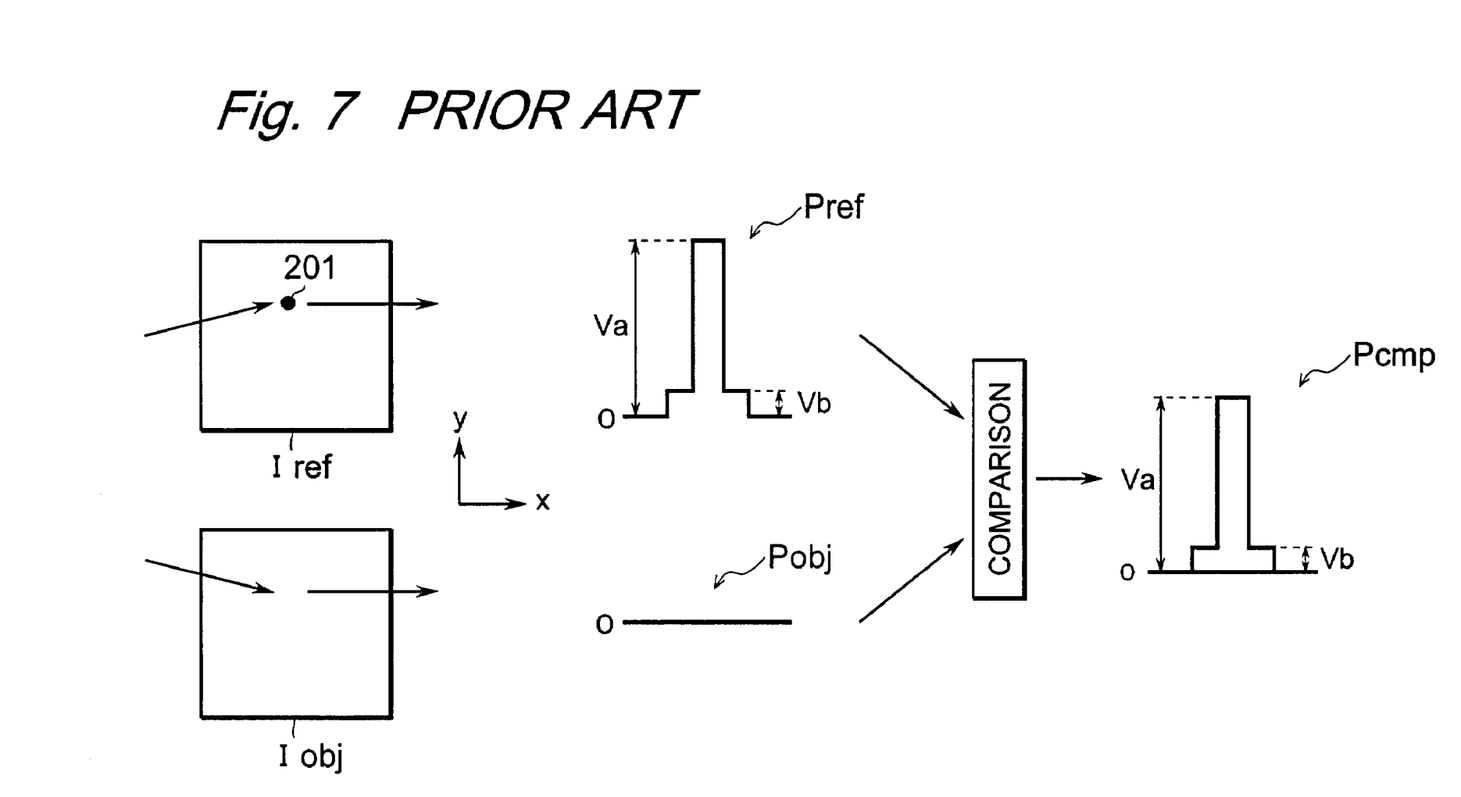
FIG. 7 describes a problem arising from applying the prior art pattern inspection method (prior art method) to an inspected object having a small pattern defect.

With the pattern inspection method taught in Japanese Patent Laid-Open Publication (kokai) 2000-65545 (below the "prior art method"), however, the pixel value range (tolerance range) set for pixels of small pattern 201 is wide when this small pattern 201 is contained in reference image Iref. More specifically, the pixel value range set for the pixel in the center of small pattern 201 (the "center pixel" below) is set based on the highest pixel value Va and the lowest pixel value Vb in the pixel group in the neighborhood of the center pixel and thus becomes a wide range as indicated by the x-axis profile Pref shown in FIG. 7 passing through small pattern 201 in reference image Iref. It should be noted that Va is the value of the center pixel in reference image Iref and the value of the pixel in the inspected object image Iobj corresponding to the center pixel is 0 in the example shown in FIG. 7, and the difference between the center pixel value and the corresponding pixel in the inspected object image Iobj (the "pixel difference" below) is therefore Va.

As noted above, the pixel value range for the center pixel is from the lowest pixel value Vb to the highest pixel value Va in the group of neighborhood pixels including the center pixel with the prior art method, and pixel values in this range Vb to Va are considered to match the pixel value of the center pixel. This means that the pixel difference at the center pixel in this case is Vb as indicated by profile Pcmp in FIG. 7. (Note that profile Pcmp combines profiles Pref and Pobj in order to compare x-axis profile Pref in reference image Iref and x-axis profile Pobj in inspected object image Iobj corresponding to profile Pref.) As will be understood from this example using reference image Iref and inspected object image Iobj and profile Pcmp, the difference detected by the comparison of the prior art method will therefore be smaller than the actual difference if a pattern defect such as a pattern loss exists in small pattern 201 of the inspected object. This means that detection sensitivity to small pattern defects drops with the prior art method due to the pixel value range setting.

Figure 8:
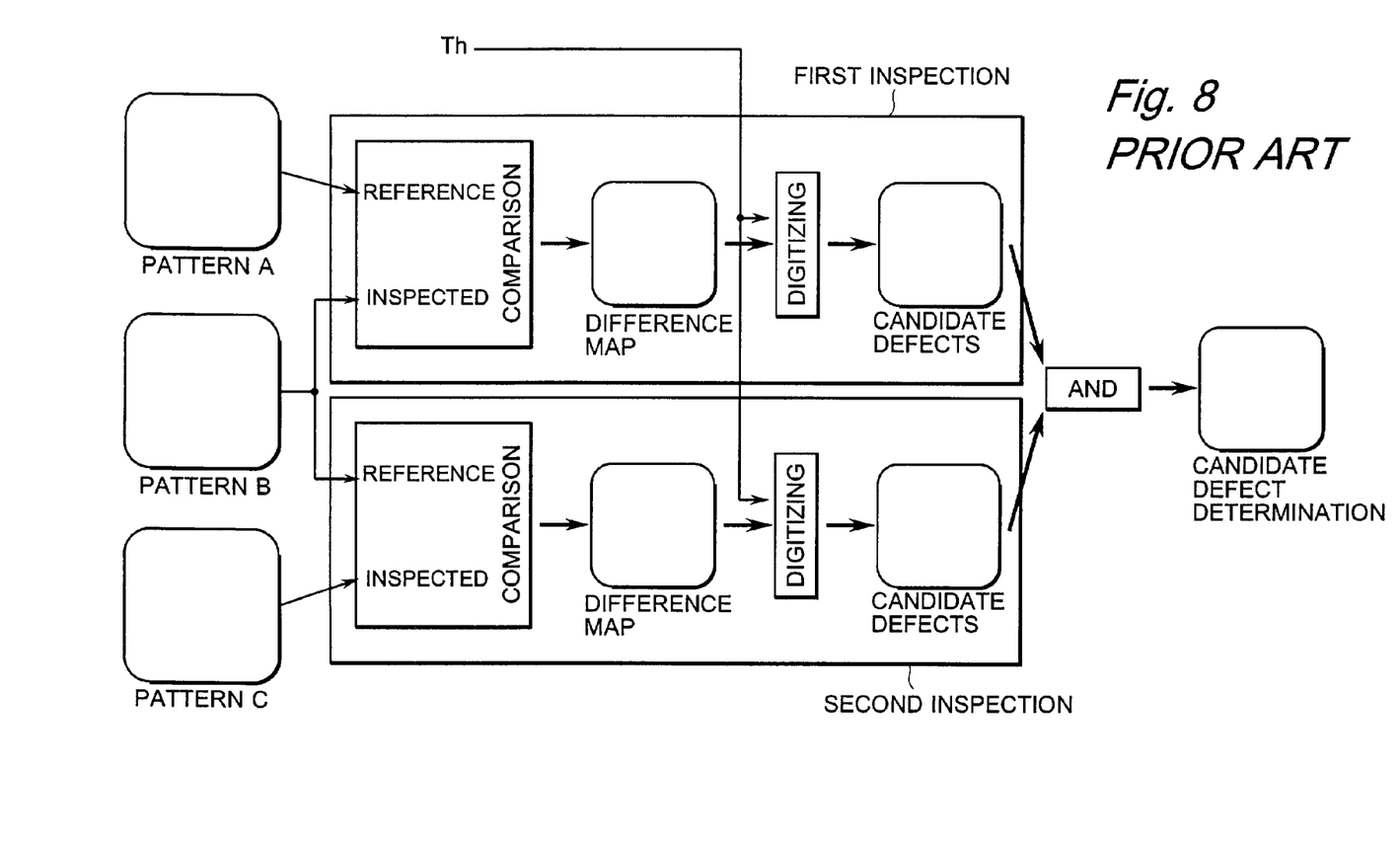
FIG. 8 describes a repeated pattern inspection method using the prior art method.

The reference image is generally replaced while inspection continues in repeated pattern inspection operations as shown in FIG. 8, but this makes it easier to miss defects when the pattern is inspected using the above prior art method. This problem is further described below with reference to FIG. 8 and FIG. 9.

Figure 9:
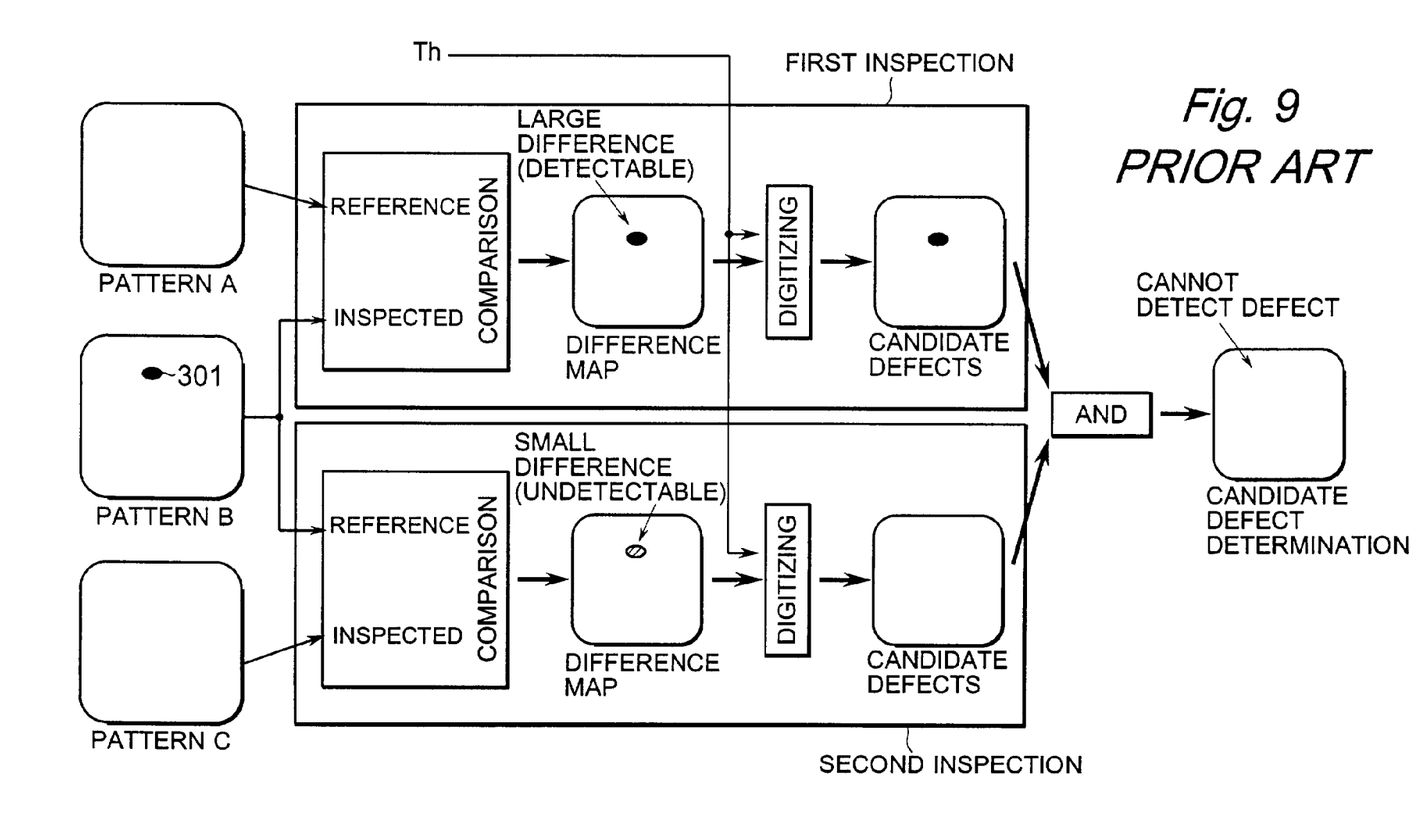
FIG. 9 describes problems when inspecting repeated patterns using the conventional comparison method (prior art method).

In the example shown in FIG. 8 repeat pattern A is first used as the reference image pattern, repeat pattern B as the pattern of the inspected object image, and a first inspection is made by comparing these repeat patterns A and B. Next, repeat pattern B is used as the reference image pattern and repeat pattern C as the pattern of the inspected object image, and, a second inspection is made by comparing patterns B and C. These first and second inspections compare the patterns of the reference image and inspected object image, generate a difference map based on the result, and determine candidate defects by binary-digitizing the difference map using a specific threshold value Th. Defects in pattern B are then identified by obtaining data equivalent to the AND of the binary data indicating the candidate defects obtained from the first and second inspections. If a small defect 301 is present in pattern B as shown in FIG. 9 in this repeated pattern inspection and a pixel value range is set for each pixel in the reference image according to the above prior art method, the value of the pixel difference for the pixels corresponding to small defect 301 will be different in the first and second inspections. As a result, if the candidate defects are obtained by binary-digitizing the difference map generated from both inspections using the same threshold value Th, defect detection sensitivity drops in the second inspection because the value of the pixel difference is lower, and it becomes easy to miss defects.

It should be noted that this problem can be avoided by suitably changing the threshold value Th used to detect candidate defects from the difference map in the first and second inspections, but in practice it is very difficult to suitably change the threshold value Th so that defects are not missed because it is not known where the defects exist.

SUMMARY OF THE INVENTION

An object of the present invention is therefore to provide an apparatus and a method for pattern inspection using a comparative method employing a multivalued image so that detection errors due to image sampling error can be avoided and defects can be reliably detected.

The present invention achieves this object as described below.

A first aspect of the present invention is a pattern inspection apparatus for generating a difference map representing differences between an inspection image and a reference image by comparing the inspection image and the reference image pixel by pixel, and detecting defects in an inspected object based on the difference map, the inspection image being a multivalued image obtained by photographing the inspected object with a specific pattern formed thereon and the reference image being a multivalued image representing the specific pattern as a reference standard, the pattern inspection apparatus comprising:

a marginal distribution feature value calculation unit for sequentially focusing on each pixel in the inspection image and a pixel at a corresponding position in the reference image, and calculating a first marginal distribution feature value indicative of spatial variation in pixel values in a neighborhood of the focus pixel in the inspection image, and a second marginal distribution feature value indicative of spatial variation in pixel values in a neighborhood of the focus pixel in the reference image;

a selection unit for selecting the inspection image focus pixel or the reference image focus pixel having less spatial variation in neighborhood pixel values as a tolerance pixel based on the first and second marginal distribution feature values, and selecting the other focus pixel as a target pixel;

a tolerance range calculation unit for calculating as a tolerance range a range of pixel values to be used as a value of the tolerance pixel allowing error in a coincidence evaluation of the inspection image focus pixel and reference image focus pixel; and a comparison unit for calculating a difference value indicative of a difference between the target pixel and tolerance pixel by comparing the target pixel with the tolerance pixel within the tolerance range, and storing the difference value to a specific memory;

the difference map being created by writing the difference values to the specific memory.

This aspect of the invention selects the focus pixel in the reference image or inspection image having the least spatial variation in neighborhood pixel values as the tolerance pixel, selects the other focus pixel as the target pixel, and sets a tolerance range for the tolerance pixel. A pixel value difference is then calculated by comparing the target pixel with the tolerance pixel within the tolerance range, and compiles a difference map showing the differences between the inspection image and reference image based on the calculated difference values. The image for which the tolerance range is set for allowing error in the coincidence evaluation determining if the value of the focus pixel in the inspection image and the value of the focus pixel in the reference image match is thus changed as needed pixel by pixel according to spatial variation in the focus pixel neighborhood, thereby improving defect detection sensitivity and making it possible to avoid detection of pseudodefects due to image sampling error. More specifically, if there is a small pattern loss in the inspected object, the focus pixel of the inspection image has little spatial variation in the neighborhood pixel values and is selected as the tolerance pixel in that small pattern part, and a wide tolerance range does not result as it does with the prior art method. Small pattern loss in the inspected object can therefore be reliably detected.

In a second aspect of the invention the feature value calculation unit preferably computes a difference between a maximum value and a minimum value in a pixel group in a neighborhood of the focus pixel in the inspection image as the first marginal distribution feature value, and computes a difference between a maximum value and a minimum value in a pixel group in a neighborhood of the focus pixel in the reference image as the second marginal distribution feature value.

With this aspect of the invention the inspection image focus pixel or reference image focus pixel having the smaller difference between maximum and minimum values in the neighborhood pixel group is selected as the tolerance pixel and the tolerance range is calculated therefor. It is therefore possible to improve defect detection sensitivity and to avoid false defect detection due to image sampling error.

In a third aspect of the invention the feature value calculation unit preferably computes a variance in pixel values of a pixel group in a neighborhood of the focus pixel in the inspection image as the first marginal distribution feature value, and computes a variance in pixel values of a pixel group in a neighborhood of the focus pixel in the reference image as the second marginal distribution feature value.

With this aspect of the invention the focus pixel having less variance in pixel values in the neighborhood pixel group is selected from the focus pixels of the inspection image and reference image as the tolerance pixel, and the tolerance range is calculated therefor. It is therefore possible to improve defect detection sensitivity and to avoid false defect detection due to image sampling error.

In a fourth aspect of the invention the tolerance range calculation unit computes the tolerance range based on a maximum value and a minimum value in a neighborhood pixel group of the focus pixel selected as the tolerance pixel.

When thus comprised the tolerance range is calculated according to the variation in pixel values in areas where there is great variation in the pixel values, such as at image edges. It is therefore possible to detect defects with good precision and to avoid false defect detection due to image sampling error.

Further preferably in this case the tolerance range calculation unit computes an upper limit of the tolerance range by interpolation based on the value of the focus pixel selected as the tolerance pixel and a highest value in the neighborhood pixel group of the focus pixel, and computes a lower limit of the tolerance range by interpolation based on the value of the focus pixel selected as the tolerance pixel and a lowest value in the neighborhood pixel group of the focus pixel.

With this fifth aspect of the invention the tolerance range is calculated according to the variation in pixel values in areas where there is great variation in the pixel values, such as at image edges. It is therefore possible to detect defects with good precision and to avoid false defect detection due to image sampling error. It is also possible to desirably adjust and balance defect detection sensitivity and detection precision because the tolerance range is determined by interpolation.

A sixth aspect of the present invention is a pattern inspection method for generating a difference map representing differences between an inspection image and a reference image by comparing the inspection image and the reference image pixel by pixel, and detecting defects in an inspected object based on the difference map, the inspection image being a multivalued image obtained by photographing the inspected object with a specific pattern formed thereon and the reference image being a multivalued image representing the specific pattern as a reference standard, the pattern inspection method comprising:

a marginal distribution feature value calculation step of sequentially focusing on each pixel in the inspection image and a pixel at a corresponding position in the reference image, and calculating a first marginal distribution feature value indicative of spatial variation in pixel values in a neighborhood of the focus pixel in the inspection image, and a second marginal distribution feature value indicative of spatial variation in pixel values in a neighborhood of the focus pixel in the reference image;

a selection step of selecting the inspection image focus pixel or the reference image focus pixel having less spatial variation in neighborhood pixel values as a tolerance pixel based on the first and second marginal distribution feature values, and selecting the other focus pixel as a target pixel;

a tolerance range calculation step of calculating as a tolerance range a range of pixel values to be used as a value of the tolerance pixels allowing error in a coincidence evaluation of the inspection image focus pixel and reference image focus pixel; and a comparison step of calculating a difference value indicative of a difference between the target pixel and tolerance pixel by comparing the target pixel with the tolerance pixel within the tolerance range, and storing the difference value to a specific memory;

the difference map being created by writing the difference values to the specific memory.

Other objects and attainments together with a fuller understanding of the invention will become apparent and appreciated by referring to the following description and claims taken in conjunction with the accompanying drawings.

DESCRIPTION OF PREFERRED EMBODIMENTS

Preferred embodiments of the present invention are described below with reference to the accompanying figures.

1. Overall Configuration of a Pattern Inspection Apparatus

Figure 1:
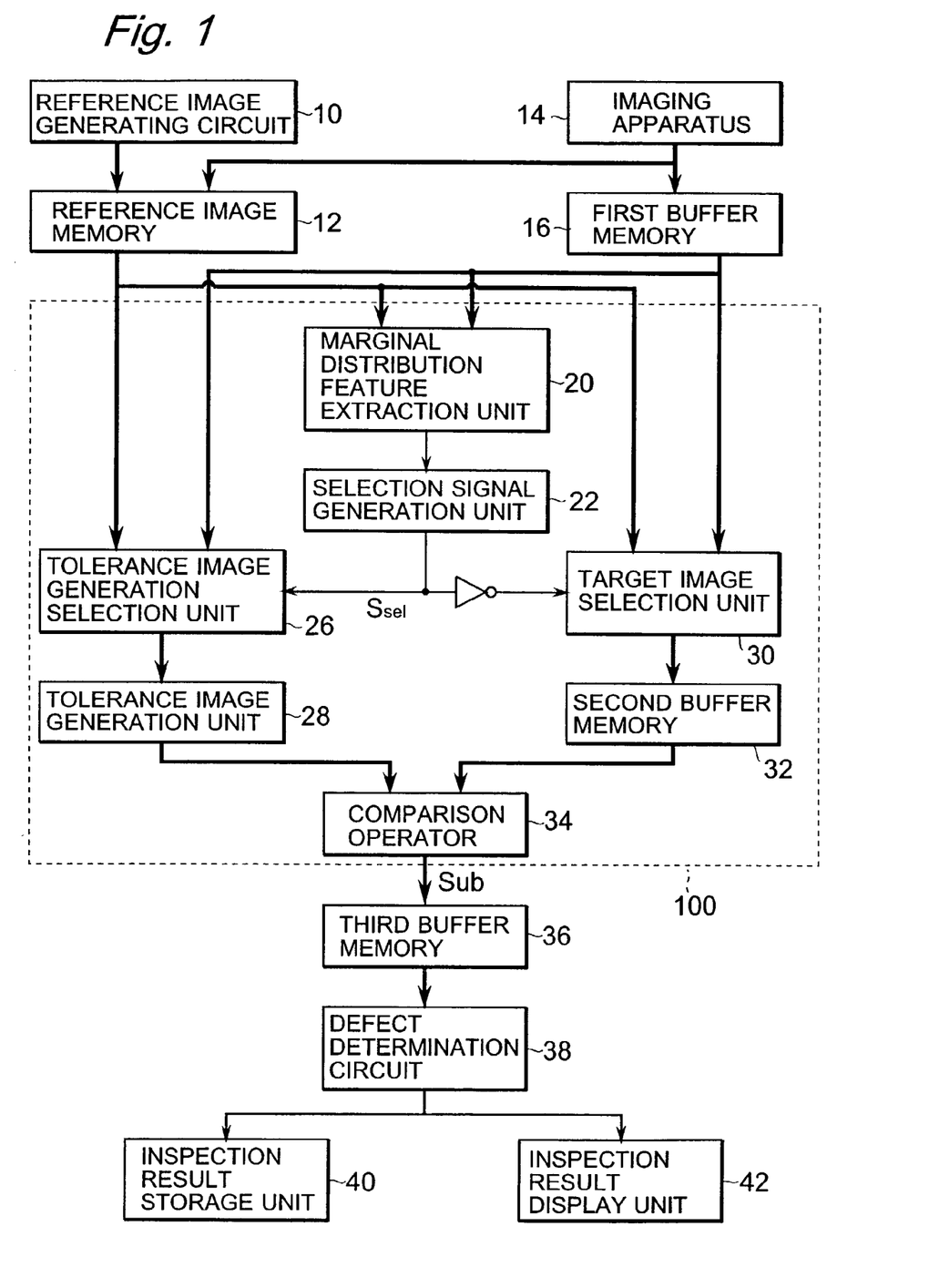
FIG. 1 is a block diagram showing the configuration of a pattern inspection apparatus according to a preferred embodiment of the present invention.

FIG. 1 is a block diagram showing the configuration of a pattern inspection apparatus according to a preferred embodiment of the present invention. This pattern inspection apparatus detects defects in an inspected object by comparing each pixel in an inspected object image and a reference image. The inspected object image is a multivalued image obtained by photographing an inspected object such as a printed wiring board or semiconductor wafer with a pattern formed on the surface thereof. The reference image is a multivalued image equivalent to an image of a good object of the same type as the inspected object. The reference image is an image used as the standard for comparing the inspected object image in order to detect defects in the inspected object, and can be generated by photographing a good object of the same type as the inspected object or it can be generated from the design data describing the pattern that should be formed on the inspected object.

As shown in FIG. 1 this pattern inspection apparatus has an imaging apparatus 14, first buffer memory 16, reference image generating circuit 10, and reference image memory 12.

The imaging apparatus 14 has, for example, a stage on which the inspected object is placed for movement in a primary scanning direction and a secondary scanning direction by means of a drive means, a CCD or other imaging device for capturing an image of the inspected object on the stage, and an A/D converter for converting the image signal output from the imaging device to a digital signal. The imaging apparatus 14 photographs the inspected object or a good (defect-free) object of the same type ("reference object" below), and outputs a digital image signal. If an inspected object is photographed by the imaging apparatus 14, a signal indicative of the inspected object image is output as the digital image signal and stored as the inspected object image data to first buffer memory 16. If the imaging apparatus 14 captures an image of a reference object, a signal indicative of the reference image is output as the digital image signal and is stored as the reference image data to the reference image memory 12.

The reference image generating circuit 10 generates reference image data from the design data for the pattern that should be formed on the inspected object, and stores the reference image data to the reference image memory 12.

The reference image memory 12 thus stores either reference image data generated by the imaging apparatus 14 from captured image data, or reference image data generated by the reference image generating circuit 10 from the design data.

This pattern inspection apparatus also has a marginal distribution feature extraction unit 20, selection signal generation unit 22, tolerance image generation selection unit 26, tolerance image generation unit 28, target image selection unit 30, and second buffer memory 32.

The marginal distribution feature extraction unit 20 sequentially focuses on two pixels (referred to below as "focus pixels"), specifically a pixel in the inspected object image and a pixel in the reference image, at corresponding positions in each image, extracts a feature of the distribution of pixel values marginal to the focus pixel in the inspected object image and extracts a feature of the distribution of pixel values marginal to the focus pixel in the reference image, and outputs a value indicative of these features as the marginal distribution feature value.

The selection signal generation unit 22 generates a selection signal Ssel based on this marginal distribution feature value. This selection signal Ssel is for selecting the reference image when spatial variation in the pixel values in the neighborhood of the focus pixel in the inspected object image is greater than spatial variation in the pixel values in the neighborhood of the focus pixel in the reference image, and selecting the inspected object image when the opposite is the case. It should be noted that either image can be selected when the spatial variation is substantially the same, and this embodiment of the invention is described as selecting the reference image by way of example.

The tolerance image generation selection unit 26 outputs the focus pixel value from the inspected object image (inspection image) or reference image selected by selection signal Ssel as the source data for tolerance image generation, and the tolerance image generation unit 28 generates a tolerance image from this source data. This tolerance image comprises tolerance pixels generated from the focus pixels of the image selected on a pixel unit basis from the reference image or inspected object image selected by selection signal Ssel, and the value of each tolerance pixel is not constant but has width. This width is equivalent to the range of pixel values ("tolerance range" below) treated as the value of a tolerance pixel for allowing error when determining a match between the focus pixel in the inspected object image and the corresponding pixel in the reference image.

Based on the inverse of selection signal Ssel, the target image selection unit 30 stores the target image data in the second buffer memory 32 by sequentially outputting the focus pixel values from the image (referred to below as the "target image"), i.e., the inspection image or reference image, that was not selected as the tolerance image.

This pattern inspection apparatus also has a comparison operator 34, third buffer memory 36, defect determination circuit 38, inspection result storage unit 40, and inspection result display unit 42.

Using a value within the tolerance range of each tolerance pixel as the value of that tolerance pixel, the comparison operator 34 compares the target image and tolerance image pixel by pixel and sequentially outputs difference Sub indicating the difference between the pixel values of each target image and tolerance image. More specifically, if the value of a pixel in the target image ("target pixel" below) is within the tolerance range of the tolerance pixel at the position corresponding to the target pixel, the output value of difference Sub is 0, and if the target pixel value is outside the tolerance range, a value indicative of how far the target pixel value is outside the tolerance range is output as the difference Sub. The difference Sub values sequentially output from the comparison operator 34 are written to the third buffer memory 36.

When difference Sub is written for every pixel in the target image to third buffer memory 36, a difference map compiling the difference between each of the pixels in the tolerance image and target image will have been created in the third buffer memory 36. This difference map can be treated as a difference image representing the differences between the inspection image and reference image.

The defect determination circuit 38 then determines a threshold value based on the difference map thus obtained, decides that a defect is present wherever the difference value in the difference map is greater than or equal to the threshold value, and outputs data indicating the pixel corresponding to the defect as the inspection result.

The inspection result storage unit 40 could be a hard disk drive, semiconductor memory, or other such storage device, and stores the inspection results received from the defect determination circuit 38.

The inspection result display unit 42 could be a CRT (Cathode-Ray Tube), LCD(Liquid Crystal Display), or other type of display device for presenting the inspection results received from the defect determination circuit 38.

2. Pixel Comparison Method Used as the Basis for the Present Embodiment

Similarly to the prior art method, this embodiment of the invention sets a pixel value range as a tolerance range for one of the two compared pixels in order to prevent detection errors resulting from image sampling error. Unlike the prior art method, however, the method of the present invention determines for each pixel whether the tolerance range is set for the reference image or inspection image. The method of this invention thus differs from the prior art method which sets the tolerance range (pixel value range) only with respect to the reference image.

The specific method of the present embodiment for setting the tolerance range also differs slightly from the prior art method.

The configuration of the present embodiment with respect to these differences is described later below after first describing the pixel comparison method (referred to below as the "pixel comparison method that is the basis for the present embodiment" or simply the "basis method") whereby the present embodiment generates a difference map from the inspected object image and reference image assuming that the tolerance range is set only with respect to the reference image as in the prior art.

Figure 2:
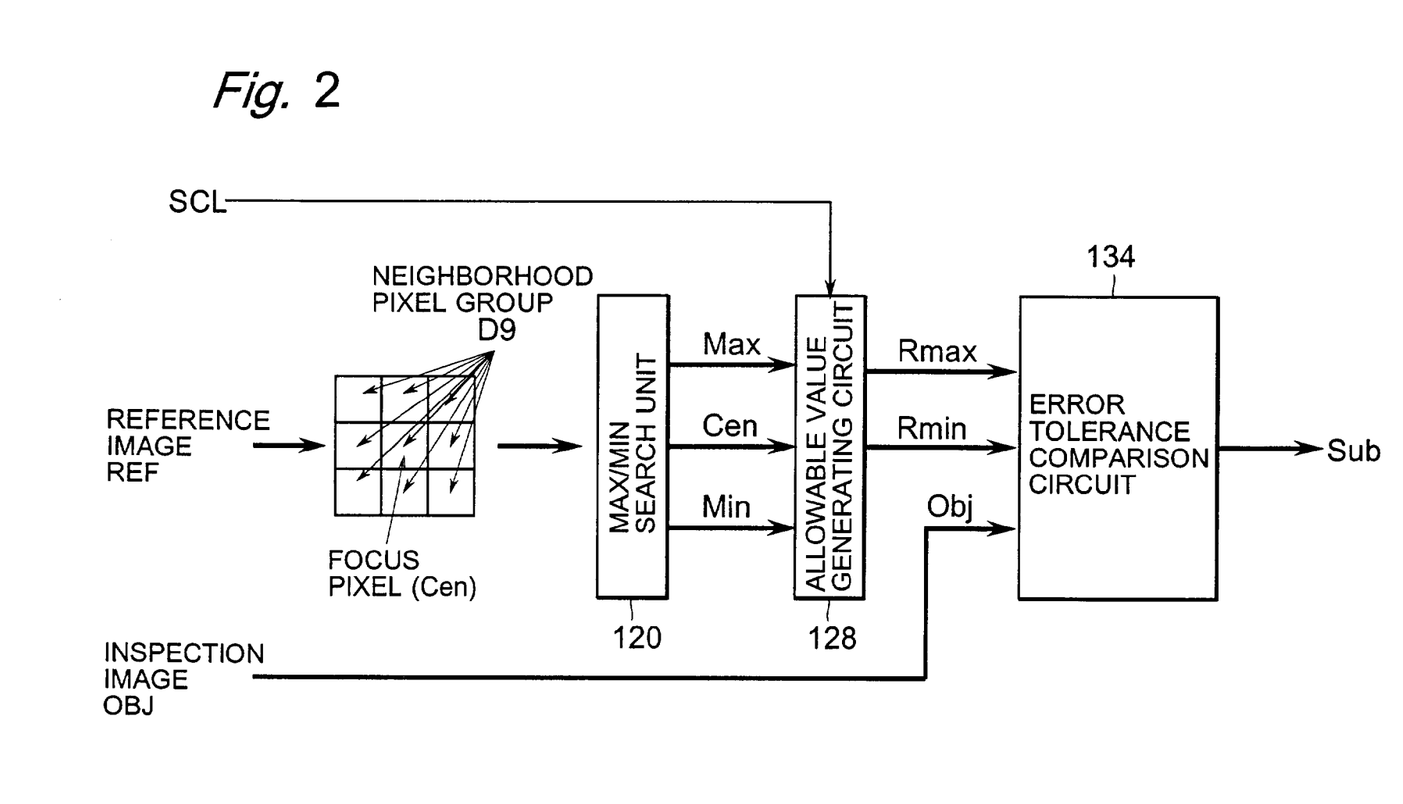
FIG. 2 is a detailed block diagram describing a method that is the basis ("basis method") for generating a difference map from the inspected object image and reference image in the preferred embodiment shown in FIG. 1.

FIG. 2 is a block diagram for describing the pixel comparison method that is the basis for the present embodiment (basis method). In this basis method the comparison processing unit 100 (corresponding to the part enclosed in a dotted line in FIG. 1) is configured as shown in FIG. 2 and has a max/min search unit 120 equivalent to the marginal distribution feature extraction unit 20, allowable value generating circuit 128 equivalent to the tolerance image generation unit 28, and error tolerance comparison circuit 134 equivalent to the comparison operator 34.

As described above this embodiment of the invention sequentially targets two pixels, a pixel in the inspected object image and a pixel in the reference image, at mutually corresponding positions in the respective images, and these two focus pixels are compared with each other. The max/min search unit 120 in this basis method obtains the highest pixel value Max and the lowest pixel value Min in the nine pixel values of the neighborhood pixel group D9 (including the focus pixel) of the focus pixel in reference image REF, and outputs these Max and Min values together with the focus pixel value Cen.

Using highest pixel value Max, lowest pixel value Min, focus pixel value Cen, and an externally supplied interpolation scale SCL, the allowable value generating circuit 128 calculates the maximum allowable value Rmax and the minimum allowable value Rmin from the following equations (where $0.0 \leq SCL \leq 1.0$).

$$Rmax = Cen \times SCL + Max \times (1-SCL) \quad (1)$$

$$Rmin = Cen \times SCL + Min \times (1-SCL) \quad (2)$$

The range Rmin to Rmax determined by the maximum allowable value Rmax and minimum allowable value Rmin thus calculated is the tolerance range set for the focus pixels of the reference image REF. Using a value in this tolerance range Rmin to Rmax as the value of the focus pixel in reference image REF, the error tolerance comparison circuit 134 compares a focus pixel in the inspection image OBJ with the focus pixel in the reference image REF, and outputs difference Sub indicating how far the focus pixel value Obj of the inspection image OBJ is outside tolerance range Rmin to Rmax. More specifically, if Rmin<Obj<Rmax, the focus pixel in the inspection image OBJ matches the focus pixel in the reference image REF and difference Sub is output set to 0; if Obj≦Rmin, Sub=Rmin−Obj is output; and if Obj≧Rmax, Sub=Obj−Rmax is output.

The tolerance range is thus set based on the values of pixels in the neighborhood of the focus pixel in the reference image and pixels in the inspection image and reference image are compared using this tolerance range in this basis method of the present invention. It is therefore possible to prevent detection errors where there is significant variation in neighborhood pixel values such as at image edges, i.e., detecting pseudodefects due to image sampling error can be prevented.

Defect detection sensitivity can also be adjusted by adjusting the interpolation scale SCL used in this method. More specifically, if the interpolation scale SCL is set to 1, there is no allowable error and the potential for false defect detection in image edge areas increases but detection sensitivity also increases. On the other hand, if the interpolation scale SCL is set to 0, the range defined by the highest and lowest pixel values in the neighborhood pixel group of the focus pixel is the tolerance range, and allowable error thus increases. Detection error in the edge areas, for example, can therefore be reliably prevented but detection sensitivity drops.

3. Pixel Comparison Method According to this Embodiment

Figure 3:
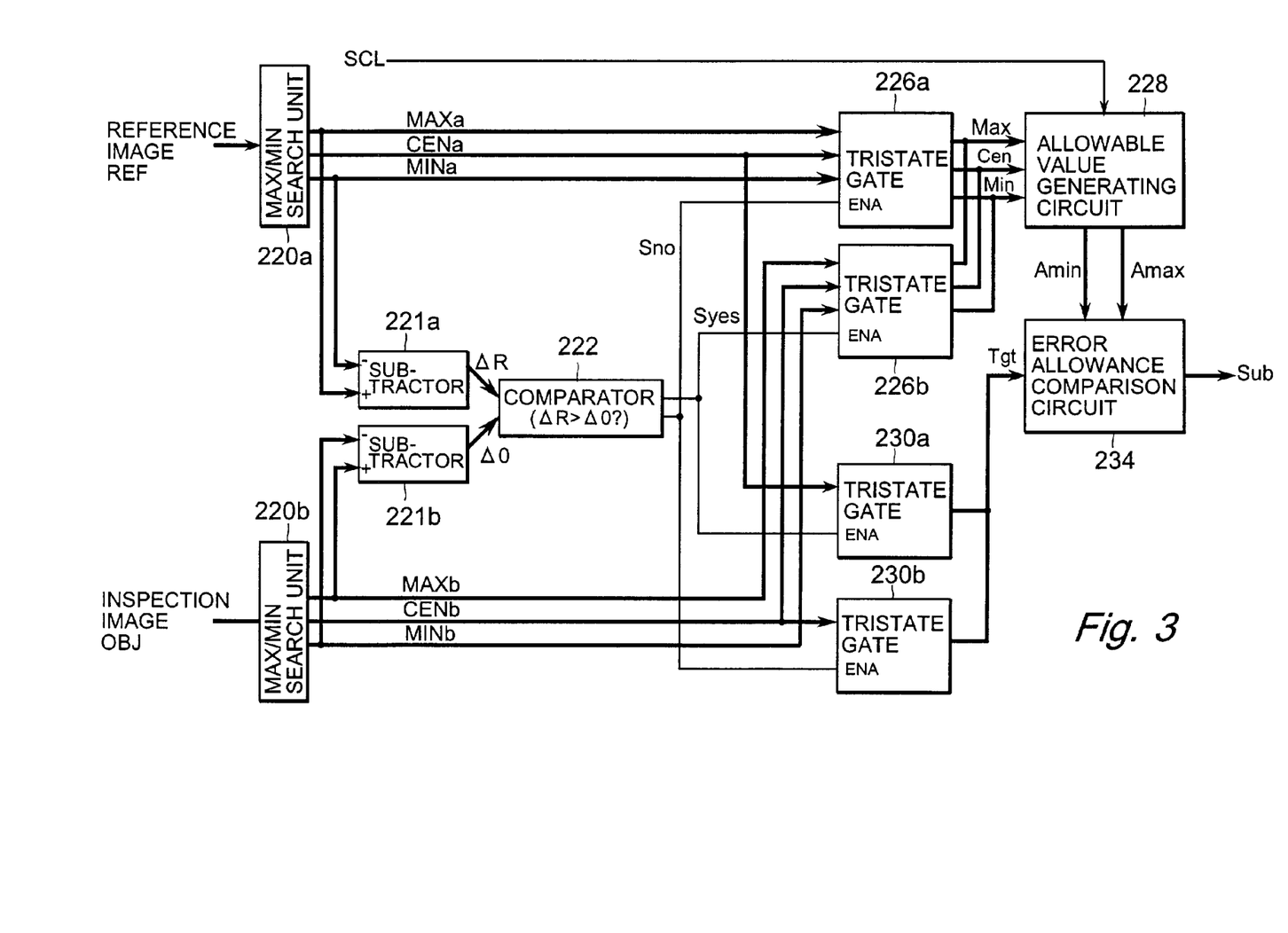
FIG. 3 is a detailed block diagram describing a pixel comparison method for generating a difference map from the inspected object image and reference image in the preferred embodiment shown in FIG. 1.

While the pixel comparison method of the present embodiment is based on the basis method described above, it further determines on a pixel basis to set the tolerance range to the reference image or inspection image, and the image data that is the basis for generating the tolerance image is switched pixel by pixel between the reference image and inspection image. FIG. 3 is a block diagram for describing a pixel comparison method according to this embodiment of the invention for producing a difference map from the inspection image OBJ and reference image REF, and shows an exemplary configuration of a comparison processing unit 100 comprising the marginal distribution feature extraction unit 20, selection signal generation unit 22, tolerance image generation selection unit 26, tolerance image generation unit 28, target image selection unit 30, second buffer memory 32, and comparison operator 34 shown in FIG. 1. More specifically, the comparison processing unit 100 of this example comprises first and second max/min search units 220a and 220b and first and second subtracters 221a and 221b forming the marginal distribution feature extraction unit 20 in FIG. 1; a comparator 222 equivalent to the selection signal generation unit 22; first and second tristate gates 226a and 226b forming tolerance image generation selection unit 26; third and fourth tristate gates 230a and 230b forming target image selection unit 30; allowable value generating circuit 228 equivalent to tolerance image generation unit 28; and error allowance comparison circuit 234 equivalent to the comparison operator 34.

The first and second max/min search units 220a and 220b in this comparison processing unit 100 are both configured identically to the max/min search unit 120 in the above-described basis method. The first max/min search unit 220a finds the highest pixel value MAXa and lowest pixel value MINa in the nine pixel values of the pixel group surrounding and including the focus pixel in the reference image REF (this group is referred to as the "focus neighborhood pixel group" below, and consists of nine pixels including the focus pixel), and outputs MAXa and MINa together with focus pixel value CENa. The second max/min search unit 220b finds the highest pixel value MAXb and lowest pixel value MINb in the nine pixel values of the focus neighborhood pixel group in the inspection image OBJ, and outputs these with the inspection image focus pixel value CENb.

The first subtracter 221a outputs the difference (MAXa−MINa) of the highest pixel value MAXa and lowest pixel value MINa output from first max/min search unit 220a as focus neighborhood change ΔR in the reference image. The second subtracter 221b outputs the difference (MAXb−MINb) of the highest pixel value MAXb and lowest pixel value MINb output from second max/min search unit 220b as focus neighborhood change ΔO in the inspection image.

The comparator 222 then determines if focus neighborhood change ΔR in the reference image is greater than focus neighborhood change ΔO in the inspection image, and outputs affirmation signal Syes or negation signal Sno indicating the result. More specifically, if ΔR>ΔO, affirmation signal Syes outputs a logic high and negation signal Sno goes to a logic low, but if ΔR≦ΔO, affirmation signal Syes goes to a logic low and negation signal Sno goes to a logic high.

The first and second tristate gates 226a and 226b each have three groups of data input terminals (i.e., first to third input terminal group), three groups of data output terminals (i.e., first to third output terminal group), and one control input terminal ENA. When a high level signal is applied to the control input terminal ENA, the signals input to the first to third input terminal group are output from the first to third output terminal group; when a low level signal is applied to the control input terminal ENA, the first to third output terminal group goes to a high impedance state.

Signals indicative of the highest pixel value MAXa, focus pixel value CENa, and lowest pixel value MINa in the focus neighborhood pixel group of the reference image REF are input to the first, second and third input terminal groups of the first tristate gate 226a, respectively. Signals indicative of the highest pixel value MAXb, focus pixel value CENb, and lowest pixel value MINb in the focus neighborhood pixel group of the inspection image OBJ are input to the first, second, and third input terminal groups of the second tristate gate 226b, respectively. The negation signal Sno is input to the control input terminal of the first tristate gate 226a, and the affirmation signal Syes is input to the control input terminal of the second tristate gate 226b. The first, second, and third output terminal groups of the first tristate gate 226a are connected to the first, second, and third output terminal groups of the second tristate gate 226b respectively, and to the first, second, and third input terminal groups of the allowable value generating circuit 228 respectively.

Therefore, if focus neighborhood change ΔR in the reference image is greater than focus neighborhood change ΔO in the inspection image, the focus pixel in the inspection image OBJ is selected as the tolerance pixel and the highest pixel value MAXb, focus pixel value CENb, and lowest pixel value MINb in the corresponding focus neighborhood pixel group are input to the allowable value generating circuit 228 as the source data, i.e., the highest pixel value Max, focus pixel value Cen, and lowest pixel value Min, used to generate the tolerance image. On the other hand, if focus neighborhood change ΔR in the reference image is less than or equal to focus neighborhood change ΔO in the inspection image, the focus pixel from the reference image REF is selected as the tolerance pixel and the highest pixel value MAXa, focus pixel value CENa, and lowest pixel value MINa in the corresponding focus neighborhood pixel group are input to the allowable value generating circuit 228 as the source data, i.e., the highest pixel value Max, focus pixel value Cen, and lowest pixel value Min, used to generate the tolerance image.

The third and fourth tristate gates 230a and 230b each have a data input terminal group, data output terminal group, and control input terminal ENA. When a high level signal is applied to the control input terminal ENA, the signals input to the data input terminal group are output from the data output terminal group. When a low level signal is applied to the control input terminal ENA the data output terminal group goes to a high impedance state. A signal indicative of the focus pixel value CENa of the reference image REF is input to the data input terminal group of the third tristate gate 230a, and a signal indicative of the focus pixel value CENb of inspection image OBJ is input to the data input terminal group of fourth tristate gate 230b. Affirmation signal Syes is input to the control input terminal of third tristate gate 230a, and negation signal Sno is input to the control input terminal of fourth tristate gate 230b. The data output terminal group of the third tristate gate 230a is connected to the data output terminal group of the fourth tristate gate 230b and to the data input terminal group of the error allowance comparison circuit 234.

Therefore, if focus neighborhood change ΔR of the reference image is greater than focus neighborhood change ΔO of the inspection image, the focus pixel in the reference image REF is selected as the target pixel, and the focus pixel value CENa is input to the error allowance comparison circuit 234 as target pixel value Tgt. However, if focus neighborhood change ΔR in the reference image REF is less than or equal to focus neighborhood change ΔO in the inspection image, the focus pixel in the inspection image OBJ is selected as the target pixel, and the focus pixel value CENb is input to the error allowance comparison circuit 234 as the target pixel value Tgt.

The allowable value generating circuit 228 is configured the same as the allowable value generating circuit 128 in the above-described basis method, and calculates maximum allowable value Amax and minimum allowable value Amin from the following equations (where $0.0 \leq SCL \leq 1.0$) based on the received highest pixel value Max, focus pixel value Cen, lowest pixel value Min, and interpolation scale SCL.

$$A\text{max} = \text{Cen} \times SCL + \text{Max} \times (1-SCL) \quad (3)$$

$$A\text{min} = \text{Cen} \times SCL + \text{Min} \times (1-SCL) \quad (4)$$

The range Amin to Amax determined by maximum allowable value Amax and minimum allowable value Amin thus calculated is the tolerance range set for the focus pixel selected as a tolerance pixel from among the focus pixels of the reference image REF and inspection image OBJ. The error allowance comparison circuit 234 uses a value in this tolerance range Amin to Amax as the value of the tolerance pixel, compares the target pixel with the tolerance pixel, and outputs difference Sub indicating how far the target pixel value Tgt is separated from the tolerance range Amin to Amax.

More specifically, if Amin<Tgt<Amax, the target pixel is considered to match the tolerance pixel and difference Sub is output as Sub=0. If Tgt≦Amin, Sub=Amin−Tgt is output, and if Tgt≧Amax, Sub=Tgt−Amax is output. The difference Sub output from the error allowance comparison circuit 234 is then stored to third buffer memory 36 as the value indicating the difference between the focus pixel in the inspection image OBJ and the corresponding focus pixel in the reference image REF.

4. Operation

An example of operation according to the basis method is described first below by way of comparison before describing the operation of the present embodiment.

Figure 4:
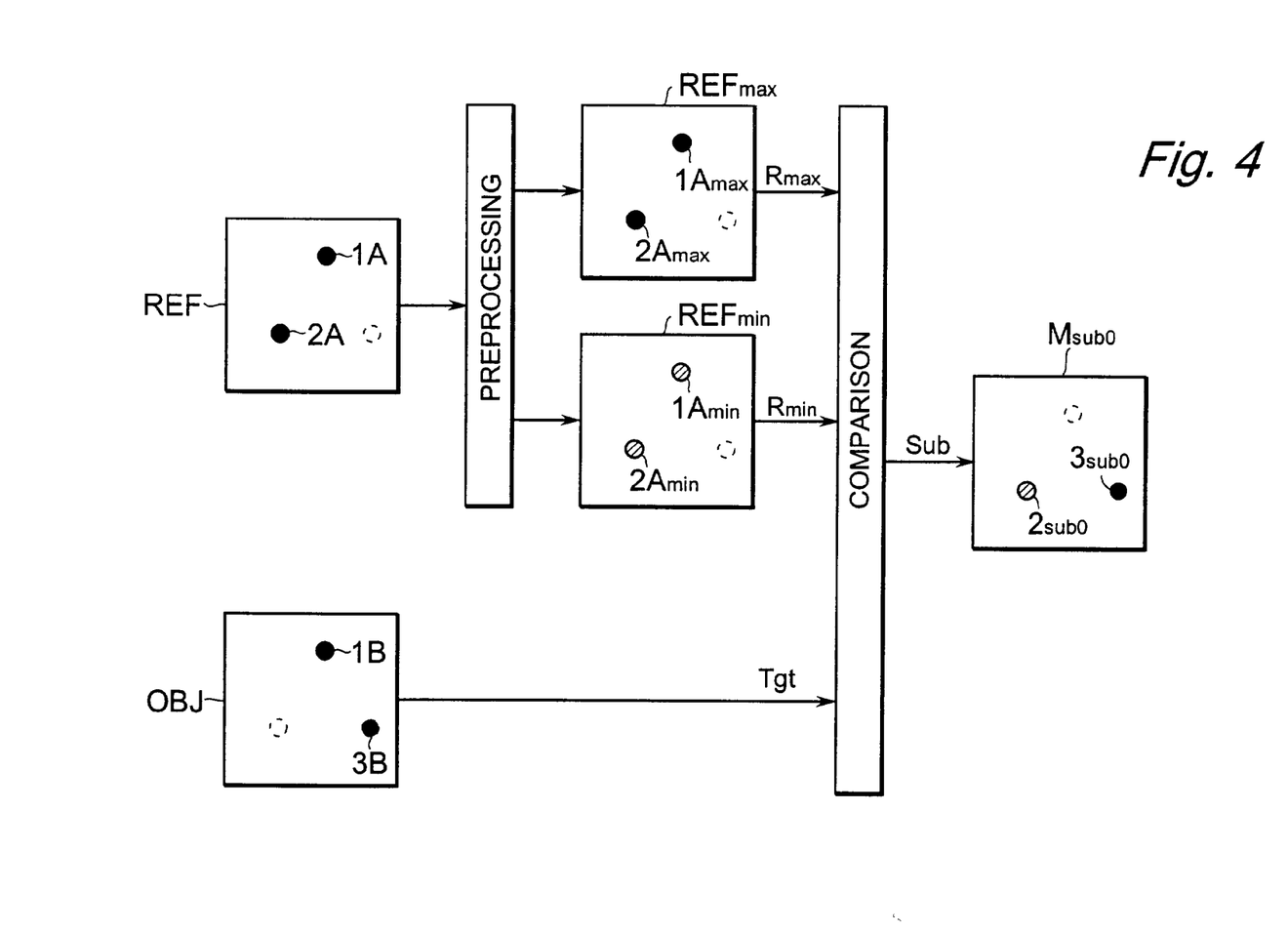
FIG. 4 describes an operating example based on the basis method for generating a difference map from the inspected object image and reference image.

FIG. 4 shows an example of applying the above-described basis method (see FIG. 2) to generate a difference map from the inspection image OBJ and reference image REF. In this example reference image REF is assumed to contain a first small pattern 1A and a second small pattern 2A, inspection image OBJ to contain a small pattern 1B corresponding to first small pattern 1A and a pattern 3B as a minute defect, and a pattern in inspection image OBJ corresponding to second small pattern 2A in the reference image REF is missing. Now consider an image REFmax (referred to below as the "maximum allowable value image") consisting of pixels each of which has the maximum allowable value Rmax calculated for each pixel in the reference image REF by allowable value generating circuit 128, and an image REFmin (referred to below as the "minimum allowable value image") consisting of pixels each of which has the minimum allowable value Rmin calculated for each pixel in the reference image REF by allowable value generating circuit 128. In this case the maximum allowable value image REFmax contains small pattern 1Amax comprising pixels with a high pixel value as a pattern equivalent to first small pattern 1A, and small pattern 2Amax comprising pixels with a high pixel value as a pattern equivalent to second small pattern 2A. The minimum allowable value image REFmin contains small pattern 1Amin comprising pixels with a low pixel value as a pattern equivalent to first small pattern 1A and small pattern 2Amin comprising pixels with a low pixel value as a pattern equivalent to second small pattern 2A.

Difference map Msub0 indicating the differences between reference image REF and inspection image OBJ is then generated by the comparison process applied by error allowance comparison circuit 234 to inspection image OBJ and reference image REF for which the allowance range is defined by maximum allowable value image REFmax and minimum allowable value image REFmin. This difference map Msub0 does not contain a pattern equivalent to the difference between first small pattern 1A in reference image REF and small pattern 1B in inspection image OBJ (Sub=0), but does contain a low pixel value pattern 2sub0 as a pattern indicating the absence of second small pattern 2A in inspection image OBJ, and a high pixel value pattern 3sub0 as a pattern equivalent to the small defect pattern 3B in inspection image OBJ. Small defects shown by this small defect pattern 3B correspond to the pattern 3sub0 comprising pixels with a high pixel value, and can therefore be detected using this difference map Msub0. The absence of small pattern 2A in inspection image OBJ, however, corresponds to the pattern 2sub0 comprising pixels with a low pixel value, and may be undetectable depending upon the setting of the threshold value used by the defect determination circuit 38. Furthermore, even if the loss of pattern 2A is detected from pattern 2sub0, it is possible that the defect indicated by the low pixel value pattern 2sub0 will be deemed not significant.

The operation of the present embodiment with respect to the inspection image OBJ and reference image REF described above is described next below.

Figure 5:
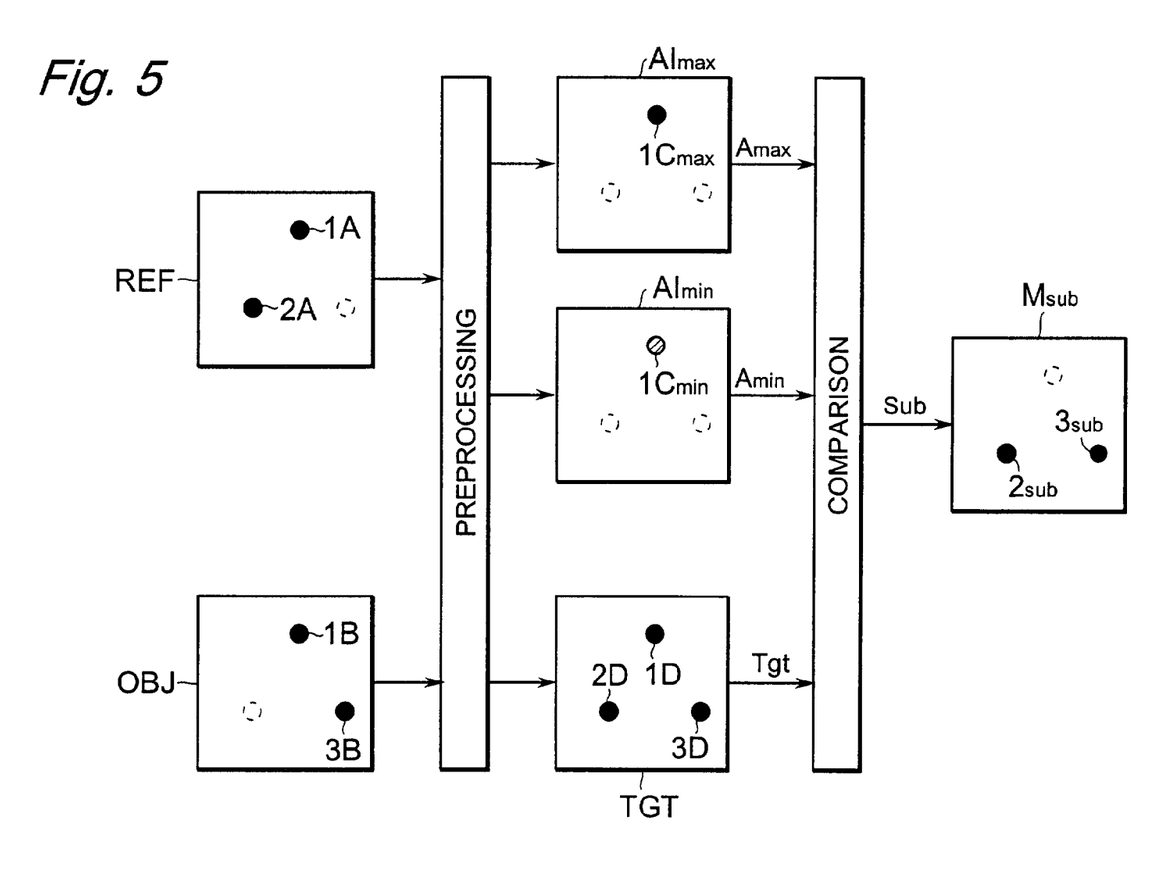
FIG. 5 describes operation of the preferred embodiment shown in FIG. 1 for generating a difference map from the inspected object image and reference image.

FIG. 5 shows an exemplary operation whereby the present embodiment (shown in FIG. 1 and FIG. 3) produces a difference map from the inspection image OBJ and reference image REF. As in the above example it is here assumed that the reference image REF contains a first small pattern 1A and a second small pattern 2A, the inspection image OBJ contains a small pattern 1B corresponding to first small pattern 1A and a small defect pattern 3B, and a pattern in inspection image OBJ corresponding to second small pattern 2A in the reference image REF is missing.

In this case a wide tolerance range Amin to Amax is set for first small pattern 1A in reference image REF even if the tolerance image is generated from the pixel values of either reference image REF or inspection image OBJ because the corresponding small pattern 1B is present in inspection image OBJ.

However, because a pattern corresponding to second small pattern 2A in reference image REF is not present in inspection image OBJ, the tolerance image is generated from the pixel values in inspection image OBJ where there is little change in the pixel values in the focus neighborhood. More specifically, both maximum allowable value Amax and minimum allowable value Amin are generated with a value near 0 based on the values of the neighborhood pixel groups of the pixels in inspection image OBJ corresponding to the pixels of the second small pattern 2A in the reference image REF.

Furthermore, because there is no pattern in the reference image REF corresponding to the small defect pattern 3B in inspection image OBJ, the tolerance image is produced from pixel values in the reference image REF with little change in the focus neighborhood. More specifically, both maximum allowable value Amax and minimum allowable value Amin are generated with a value near 0 based on the values of the neighborhood pixel groups of the pixels in reference image REF corresponding to the pixels of defect pattern 3B in inspection image OBJ.

As is the case with the basis method, consider a maximum allowable value image AImax consisting of pixels each of which has the maximum allowable value Amax calculated for each tolerance pixel, and a minimum allowable value image AImin consisting of pixels each of which has the minimum allowable value Amin calculated for each tolerance pixel. In this case the maximum allowable value image AImax contains small pattern 1Cmax of pixels with a high pixel value as a pattern equivalent to first small pattern 1A, but does not contain a pattern equivalent to second small pattern 2A (or if it does, the pattern contains pixels with quite low pixel values). In addition, the minimum allowable value image AImin contains a small pattern 1Cmin of pixels with low pixel values, but does not contain a pattern equivalent to second small pattern 2A (or if it does, the pattern contains pixels with quite low pixel values). It should be noted that a pattern equivalent to small defect pattern 3B is not included in minimum allowable value image AImin or maximum allowable value image AImax. The tolerance image comprises the pixels selected as the tolerance pixels from among the focus pixels in the inspection image OBJ and reference image REF, and a tolerance range defined by maximum allowable value image AImax and minimum allowable value image AImin is set for each pixel in the tolerance image.

The target image TGT comprises the pixels selected from the focus pixels in reference image REF and inspection image OBJ with a high (or more accurately a not-low) focus neighborhood change value, and therefore contains a small pattern 1D of pixels with a high pixel value as a pattern equivalent to small pattern 1A or 1B, a small pattern 2D of pixels with a high pixel value as a pattern equivalent to second small pattern 2A, and a small pattern 3D of pixels with a high pixel value as a pattern equivalent to small defect pattern 3B.

Difference map Msub indicating the differences between reference image REF and inspection image OBJ is then obtained when the error allowance comparison circuit 234 processes target image TGT and the tolerance image, which comprises tolerance pixels having a tolerance range thus defined by maximum allowable value image AImax and minimum allowable value image AImin. A pattern equivalent to the differences between first small pattern 1A in reference image REF and small pattern 1B in inspection image OBJ is not present (Sub=0) in this difference map Msub, but pattern 2sub comprising pixels with a high pixel value as a pattern indicative of the absence in inspection image OBJ of the pattern corresponding to second small pattern 2A in reference image REF, and pattern 3sub comprising pixels with a high pixel value as a pattern equivalent to small defect pattern 3B in inspection image OBJ, are present in the difference map Msub.

It is therefore possible using this difference map Msub to reliably detect both the loss of second small pattern 2A and small defects represented by pattern 3B in the inspection image OBJ representing the inspected object.

5. Benefits of the Invention

As will be known from the preceding description, instead of setting a tolerance range only for the reference image, this embodiment of the present invention based on the above pixel comparison method sequentially selects from among the focus pixels of the reference image and inspection image the pixel having less change ($\Delta R$, $\Delta O$) in the focus neighborhood as the tolerance pixel forming the tolerance image, sets a tolerance range Amin to Amax for the tolerance pixel, and selects from among the focus pixels in the reference image and inspection image the pixel for which a tolerance range is not set as the target pixel forming the target image. A value in the tolerance range Amin to Amax is then used as the value of that tolerance pixel for an error allowance comparison process applied to the target image and tolerance image. Because the image used to set the tolerance range is switched on a pixel unit basis according to change ($\Delta R$, $\Delta O$) in the focus neighborhood, it is possible to avoid detecting pseudodefects caused by image sampling error as in the basis method, and it is also possible to suppress a drop in detection sensitivity.

More specifically, when a reference image containing a small pattern is compared with an inspection image in which that small pattern is missing, a tolerance range is set for each focus pixel in the inspection image corresponding to the small pattern before the small pattern parts are compared in the reference and inspection images so that the difference Sub for these small pattern parts is sufficiently high. Because this difference Sub is also stored in third buffer memory 36 as a value indicative of the difference between the reference image and inspection image in this small pattern part, defects apparent as the loss of a small pattern in the inspection object can be reliably detected.

Furthermore, because the image for which a tolerance range is set for the comparison of the inspection image and reference image is switched pixel by pixel dynamically according to change in the focus neighborhood, this embodiment of the invention enables robust defect detection with detection precision and detection sensitivity minimally dependent on pattern shape. It should be noted that because a tolerance range is set for each pixel in the tolerance image, the present invention can, similarly to the prior art method, detect defects without precise registration for the image comparison.

Furthermore, because the image for which the tolerance range is set for the error allowance comparison is changed by pixel unit in the present embodiment, the image comparison operation obtains the difference between both images without distinguishing between the reference image and inspection image. Therefore, when inspecting repeated patterns while changing the reference image (see FIG. 8 and FIG. 9), detection sensitivity does not change due to changing the reference image as it does with the prior art method, and the present invention is therefore able to prevent not finding a defect.

6. Alternative Embodiment

The preceding embodiment determines whether to set the tolerance range for the focus pixel in the inspection image or the focus pixel in the reference image (i.e., which focus pixels to use to generate the tolerance image) based on a marginal distribution feature value, and uses focus neighborhood change $\Delta R$ or $\Delta O$, which is the difference between the highest and lowest pixel values in the group of nine pixels surrounding and including the focus pixels in both images, as this marginal distribution feature value (see FIG. 3).

The marginal distribution feature value used to determine the focus pixel for which the tolerance range is set is not, however, limited to this value ($\Delta R$, $\Delta O$) representing change in the pixel values in the focus neighborhood. Spatial variation in the pixel values near the focus pixel could, for example, be used. The variance of the nine pixel values near the focus pixel can therefore be used as the marginal distribution feature value instead of focus neighborhood change $\Delta R$ or $\Delta O$. The number of pixels used to calculate this variance or other marginal distribution feature value is also not limited to the nine adjacent pixels. A block of 5×5=25 pixels around the focus pixel can, for example, be used to calculate the marginal distribution feature value.

Figure 6:
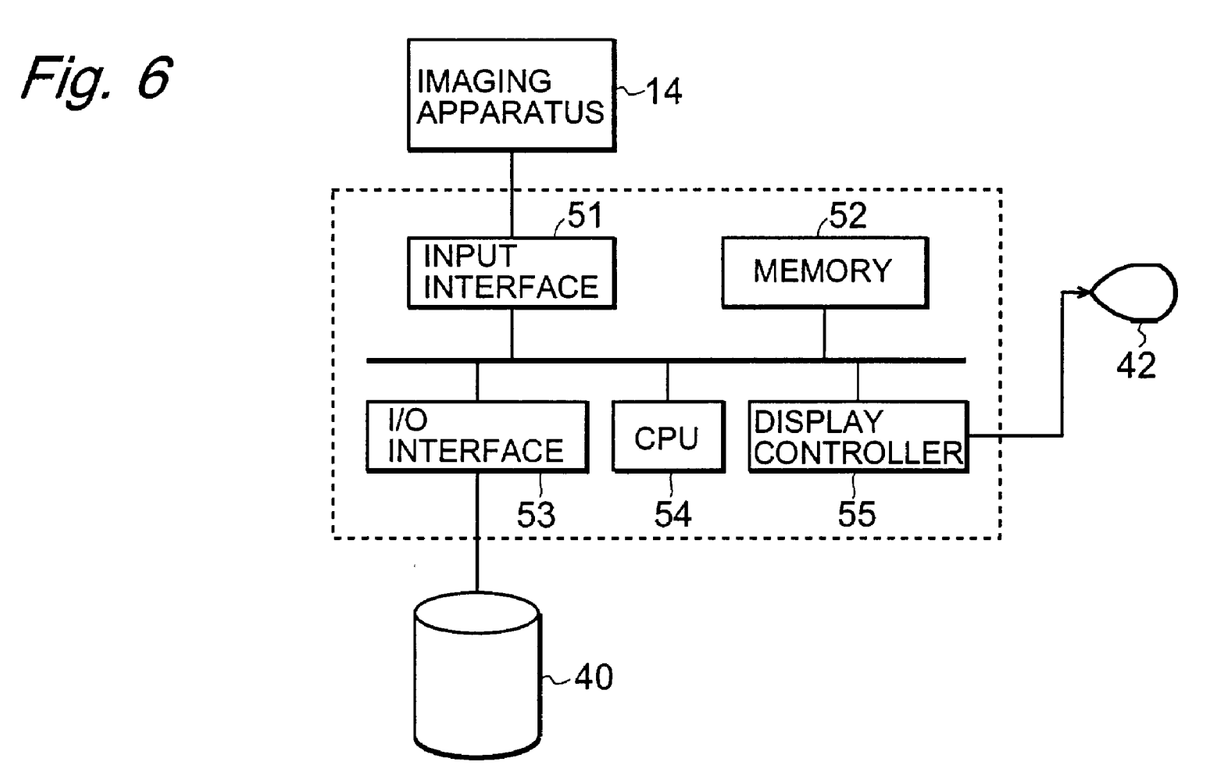
FIG. 6 is a block diagram showing the configuration of a pattern inspection apparatus according to an alternative embodiment of the present invention.

It will also be noted that a pattern inspection apparatus according to this embodiment of the invention is described as a dedicated hardware configuration, but all or part of the comparison processing unit 100 and defect determination circuit 38 shown in FIG. 1 and FIG. 3, for example, can be achieved as software configurations by running a specific program using a CPU (central processing unit). In this case, as shown in FIG. 6 the pattern inspection apparatus of the present invention can be achieved with a computer having connected via a bus a CPU 54 for running this specific program, memory 52 for storing the specific program, reference image data, and inspection image data, an input interface unit 51 to which an imaging apparatus 14 for photographing the inspection image, for example, is connected, an I/O interface unit 53 to which a hard disk drive is connected as the inspection result storage unit 40, and a display control unit 55 to which a CRT, LCD, or other display device is connected as the inspection result display unit 42.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

It will be further noted that priority for the present invention is claimed based on Japanese Patent Application 2001-245354 titled "pattern inspection apparatus and method" and filed on Aug. 13, 2001, the entire content of which is incorporated herein by reference.

What is claimed is:

1. A pattern inspection apparatus for generating a difference map representing differences between an inspection image and a reference image by comparing the inspection image and the reference image pixel by pixel, and detecting defects in an inspected object based on the difference map, the inspection image being a multivalued image obtained by photographing the inspected object with a specific pattern formed thereon and the reference image being a multivalued image representing the specific pattern as a reference standard, the pattern inspection apparatus comprising:

a marginal distribution feature value calculation unit for sequentially focusing on each pixel in the inspection image and a pixel at a corresponding position in the reference image, and calculating a first marginal distribution feature value indicative of spatial variation in pixel values in a neighborhood of the focus pixel in the inspection image, and a second marginal distribution feature value indicative of spatial variation in pixel values in a neighborhood of the focus pixel in the reference image;

a selection unit for selecting the inspection image focus pixel or the reference image focus pixel having less spatial variation in neighborhood pixel values as a tolerance pixel based on the first and second marginal distribution feature values, and selecting the other focus pixel as a target pixel;

a tolerance range calculation unit for calculating as a tolerance range a range of pixel values to be used as a value of the tolerance pixel allowing error in a coincidence evaluation of the inspection image focus pixel and reference image focus pixel; and a comparison unit for calculating a difference value indicative of a difference between the target pixel and tolerance pixel by comparing the target pixel with the tolerance pixel within the tolerance range, and storing the difference value to a specific memory;

the difference map being created by writing the difference values to the specific memory.

2. A pattern inspection apparatus according to claim 1, wherein the marginal distribution feature value calculation unit computes a difference between a maximum value and a minimum value in a pixel group in a neighborhood of the focus pixel in the inspection image as the first marginal distribution feature value, and computes a difference between a maximum value and a minimum value in a pixel group in a neighborhood of the focus pixel in the reference image as the second marginal distribution feature value.

3. A pattern inspection apparatus according to claim 1, wherein the marginal distribution feature value calculation unit computes a variance in pixel values of a pixel group in a neighborhood of the focus pixel in the inspection image as the first marginal distribution feature value, and computes a variance in pixel values of a pixel group in a neighborhood of the focus pixel in the reference image as the second marginal distribution feature value.

4. A pattern inspection apparatus according to claim 1, wherein the tolerance range calculation unit computes the tolerance range based on a maximum value and a minimum value in a neighborhood pixel group of the focus pixel selected as the tolerance pixel.

5. A pattern inspection apparatus according to claim 4, wherein the tolerance range calculation unit computes an upper limit of the tolerance range by interpolation based on the value of the focus pixel selected as the tolerance pixel and a highest value in the neighborhood pixel group of the focus pixel, and computes a lower limit of the tolerance range by interpolation based on the value of the focus pixel selected as the tolerance pixel and a lowest value in the neighborhood pixel group of the focus pixel.

6. A pattern inspection method for generating a difference map representing differences between an inspection image and a reference image by comparing the inspection image and the reference image pixel by pixel, and detecting defects in an inspected object based on the difference map, the inspection image being a multivalued image obtained by photographing the inspected object with a specific pattern formed thereon and the reference image being a multivalued image representing the specific pattern as a reference standard, the pattern inspection method comprising:

a marginal distribution feature value calculation step of sequentially focusing on each pixel in the inspection image and a pixel at a corresponding position in the reference image, and calculating a first marginal distribution feature value indicative of spatial variation in pixel values in a neighborhood of the focus pixel in the inspection image, and a second marginal distribution feature value indicative of spatial variation in pixel values in a neighborhood of the focus pixel in the reference image;

a selection step of selecting the inspection image focus pixel or the reference image focus pixel having less spatial variation in neighborhood pixel values as a tolerance pixel based on the first and second marginal distribution feature values, and selecting the other focus pixel as a target pixel;

a tolerance range calculation step of calculating as a tolerance range a range of pixel values to be used as a value of the tolerance pixels allowing error in a coincidence evaluation of the inspection image focus pixel and reference image focus pixel; and a comparison step of calculating a difference value indicative of a difference between the target pixel and tolerance pixel by comparing the target pixel with the tolerance pixel within the tolerance, and storing the difference value to a specific memory;

the difference map being created by writing the difference values to the specific memory.

7. A pattern inspection method according to claim 6, wherein the marginal distribution feature value calculation step includes:

a step of computing a difference between a maximum value and a minimum value in a pixel group in a neighborhood of the focus pixel in the inspection image as the first marginal distribution feature value; and a step of computing a difference between a maximum value and a minimum value in a pixel group in a neighborhood of the focus pixel in the reference image as the second marginal distribution feature value.

8. A pattern inspection method according to claim 6, wherein the marginal distribution feature value calculation step includes:

a step of computing a variance in pixel values of a pixel group in a neighborhood of the focus pixel in the inspection image as the first marginal distribution feature value; and a step of computing a variance in pixel values of a pixel group in a neighborhood of the focus pixel in the reference image as the second marginal distribution feature value.

9. A pattern inspection method according to claim 6, wherein the tolerance range calculation step is such that the tolerance range is calculated based on a maximum value and a minimum value in a neighborhood pixel group of the focus pixel selected as the tolerance pixel.

10. A pattern inspection method according to claim 9, wherein the tolerance range calculation step includes:

a step of computing an upper limit of the tolerance range by interpolation based on the value of the focus pixel selected as the tolerance pixel and a highest value in the neighborhood pixel group of the focus pixel; and a step of computing a lower limit of the tolerance range by interpolation based on the value of the focus pixel selected as the tolerance pixel and a lowest value in the neighborhood pixel group of the focus pixel.

* * * * *